United States Patent
Dittgen et al.

(10) Patent No.: US 6,884,793 B2
(45) Date of Patent: Apr. 26, 2005

(54) COMBINATION PREPARATION FOR CONTRACEPTION BASED ON NATURAL ESTROGENS

(75) Inventors: Michael Dittgen, Apolda (DE); Sabine Fricke, Jena (DE); Herbert Hoffmann, Jena (DE); Claudia Moore, Jena (DE); Michael Oettel, Jena (DE); Monika Ostertag, Göttingen (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/950,915

(22) Filed: Sep. 12, 2001

(65) Prior Publication Data

US 2002/0107229 A1 Aug. 8, 2002

Related U.S. Application Data

(62) Division of application No. 09/648,858, filed on Aug. 25, 2000, now abandoned, which is a continuation of application No. 08/738,314, filed on Oct. 25, 1996, now Pat. No. 6,133,251.

(30) Foreign Application Priority Data

Oct. 28, 1995 (DE) .......................................... 195 40 253

(51) Int. Cl.$^7$ .............................................. A61K 33/56
(52) U.S. Cl. ........................ 514/170; 514/178; 514/182
(58) Field of Search ................................ 514/170, 178, 514/182, 171, 843

(56) References Cited

PUBLICATIONS

English abstract of DE 4308406, CAPLUS, AN1994:491884.*
Darney, P. Safety and efficacy of a triphasic oral contraceptive containing desogestrel: Results of three multicenter trials, EMBASE abstract, AN 93302272, 1993.*
Ehrlich et al. Oral contraceptive, WPIDS abstract AN 1992–269924 (1992).*
New preparation for HRT and oral contraception, WPIDS abstract AN 1995–123225 (1995).*
J.V. Wright, et al: "Comparative Measurements of Serum Estriol, Estradio . . . ", Altern. Med. Rev. (U.S.), 4 (4), Aug. 1999, pp. 266–270.

* cited by examiner

*Primary Examiner*—San-ming Hui
(74) *Attorney, Agent, or Firm*—Michael J. Striker

(57) ABSTRACT

The combination preparation for contraception includes from 2 to 4 first stage daily dosage portions each including an effective amount of at least one natural estrogen as sole active ingredient, from 16 to 22 second stage daily dosage portions each including an effective amount of a combination of at least one natural estrogen and at least one natural or synthetic gestogen as active ingredient; from 2 to 4 third stage daily dosage portions each including an effective amount of at least one natural estrogen as sole active ingredient; and from 2 to 4 final stage daily dosage portions containing a pharmaceutically acceptable placebo. The estrogen may be estradiol, an estradiol compound that is metabolized to estradiol when taken into the body, a conjugated equine estrogen or a phytoestrogen. The natural or synthetic gestogen can be natural progesterone or a synthetic gestogens, such as medroxyprogesterone acetate.

5 Claims, No Drawings

COMBINATION PREPARATION FOR CONTRACEPTION BASED ON NATURAL ESTROGENS

CROSS-REFERENCE

This is a Division of U.S. patent application No. 09/648,858 filed Aug. 25, 2000 now abandoned, continuation under 37 C.F.R. 1.53 of U.S. patent application Ser. No. 08/738,314, filed Oct. 25, 1996, now U.S. patent No. 6,133,251 which has now been allowed.

BACKGROUND OF THE INVENTION

The present invention relates to a multistage contraceptive preparation based on natural estrogens.

Oral contraceptives were first marketed 60 years ago. By continuous research it has been possible to reduce the required dosages of hormones in a stepwise manner. Currently low dosage oral contraceptives exist which chiefly comprise an estrogen component and a gestogen component. The hormone dosage of these contraceptives is delivered in different combinations and dosages in the form of combination preparations (one-stage preparation) or multistage combination preparations (staged preparations) and sequenced preparations (two-stage preparations) over time periods of from 21 to 28 days.

One-stage preparations (usually designated as combination preparations) are characterized by a constant dosage of certain estrogens and gestogens each day. Because of the uniform delivery of gestogen ingredients with estrogen components from the first application day, the combination preparation is a highly reliable contraceptive.

The ovulatory LH-peak is reliably suppressed with all forms of combination preparation so that both ovulation and Corpus luteum formation are suppressed (M. Elstein, et al, "Studies on low dose oral contraceptives: cervical mucus and plasma hormone changes in relation to circulating d-nogestrel and 17-ethinyl estradiol concentrations", in Fertil Steril. 27, p. 892, 1976; Kontrazeption mit Hormonen (trans: Contraception with Hormones), H. D. Taubert and H. Kuhl, eds., Georg Thieme Verlag, Stuttgart/New York, 1965). Of course early secretion changes of the still weakly developing endometrium can cause intervening bleeding above all in the first cycle under the influence of a gestogen.

Modified combination or multistage preparations currently include two-stage preparations and three-stage preparations. Two-stage preparations are those, which contain a gestogen dosage, which is reduced in comparison to the conventional combination preparation, which is increased in the second stage (cycle half). A stage with a lowered gestogen dosage lasting for 11 days follows in a 21/22 day pill regime, while the estrogen dosage remains the same over the administration period.

Three-stage preparations contain lowered gestogen dosages as well as lowered estrogen dosages in the first delivery stage, which increases in two stages to its highest gestogen dosage in the last 7 to 10 days, while the estrogen ingredient is increased either uniformly or briefly during the middle of the cycle over a duration of 5 to 6 days analogously to the normal physiological cycle. Three-stage preparations allow the entire dosage of gestogens to be maintained at a lower lever than in other oral contraceptives (L. Carlborg, "Comparison of contraceptive acceptability of levonorgestrel and ethinyl oestradiol administered in a three-stage (trionetta) and a one-stage (neoletta) version", in Contraception 27, p. 5, 1983).

Two-staged preparations (sequenced preparations) contain a pure estrogen component in the first 7 to maximum 11 days of use and additionally a gestogen ingredient in the following 10 to 14 days. Because of that the endometrium is subjected to changes which very closely correspond to the normal physiological cycle. They therefore provide very good cycle control. Sequence preparations lower the basal gonadotropin level in a manner similar to combination preparations, in which the FSH-level is more strongly suppressed or lowered than the LH-level (K.AKTORIES, et al, "Die Beeinflussung des Ovarialzyklus durch verschiedene Typen hormonaler Kontrazeptiva (trans: The effect of different types of hormonal contraceptives on ovarian cycles)" in Geburtshilfe Frauenheilkunde 36, P. 318, 1976).

All currently known combination preparations for oral contraception contain ethinyl estradiol or its 3-methyl ester, mestranol, as estrogen ingredient. The latter compound is a prodrug and is metabolized in the body to ethinyl estradiol. Ethinyl estradiol has, among other things, a series of disadvantages and side effects. This synthetic estrogen is rapidly resorbed in the stomach and intestinal tract, however, because it is easily metabolized, it is rapidly absorbed already in the mucous membrane of the small intestine and/or rapidly changes chemically as a result. Besides this process has large individual variations. Hence unsatisfactory and large individual differences of bioavailability of ethinyl estradiol result. Ethinyl estradiol causes suicidal blockage of the Cytochrome P-450 system (F. P. Guengerich, "Oxidation of alpha-ethinyl estradiol by human liver Cytochrome P-450", in Molec. Pharmacol. 33, p.500, 1988; R. Bocker, et al, "In vitro interaction of contraceptive steroids with human liver Cytochrome P-450 enzymes, Advances Contraception 7, p.140, 1991) and inhibits its own metabolism. Since gestogens and a series of other foreign materials/ medications in large part are converted by the same decomposition paths, the repeated application of ethinyl estradiol-containing contraceptives can lead to an accumulation of certain xenobiotics in the body. Furthermore ethinyl estradiol has carcinogenic properties (B. T. Zhu, et al, "The carcinogenic activity of ethinyl estrogens is determined by both their hormonal characteristics and their conversion to catechol metabolites" in Endocrinol. 132, p. 577, 1993).

The general administration of natural estrogens is suggested as an alternative to ethinyl estradiol in German Patent Applications DE 41 04 385 and DE 42 24 534.

A contraceptive administration system is known from U.S. Pat. No. 4,921,843, in which a placebo is taken between the last day's dosage of the second component and the first day's dosage of the first component. This contraceptive administration system has the disadvantage that follicle maturation begins during the administration of the placebos.

The sole administration of natural estrogens has currently not found a practical application. Thus H. D. Taubert and H. Kuhl (Kontrazeption mit Hormonen, H. D. Taubert and H. Kuhl, Eds., Georg Thieme Verlag, Stuttgart, New York, 1995) fail to suggest the use of natural estradiols as estrogen ingredients in oral contraceptives. While the gestogen ingredients alone provide a reliable contraceptive protection, the proliferation of the endometrium by the natural estrogen is insufficient. A bleeding anomaly such as intervening bleeding results up to the blood-free cycles.

Up to now difficulties have occurred in experiments to develop a so-called "semi-natural pill" based on natural estrogens (e.g. micronized 17β-estradiol, natural 17β-estradiol esters, conjugated estrogens, phytoestrogens and estrone, estriol and their derivatives). For example the combination of estradiol (estradiol valerate 1 mg and/or 2 mg administered for 10 and/or 11 days) and cyproterone acetate (1 mg and/or 2 mg for 10 to 11 days) caused 33% intervening bleeding (E. HIRVONEN, et al, in "Oral Contraceptive-containing natural estradiol for premenopausal women", in Maturitas 21, p. 27, 1995) or the combination of estradiol (3 mg) and desogestrel (0.150 mg) for 21 days caused 30% intervening bleeding (H. Coelingh Bennink, "Research in Contraception", 10th Congress of the European Association of Gynecologists and Obstetricians, 1995).

Preliminary experiments for the instant invention were performed with constant estradiol dosages over 28 days and constant gestogen dosages over 24 days as well as with different estradiol dosages (2.0 mg, 4.0 mg and 2.0 mg over 7, 14 and 7 days respectively) and constant gestogen dosages over 21 days. These studies failed because the intervening bleeding rate of 25% was not substantially different from that already known from the studies of E. Hirvonen and H. Coelingh Bennink (E. Schleussner, Jenapharm GmbH Report, 1995).

SUMMARY OF THE INVENTION

It is an object of the present invention to provide a hormonal contraceptive whose administration substantially improves cycle bleeding behavior, maintains the contraceptive action of the estrogen/gestogen combination and minimizes or prevents undesirable side effects (carcinogenic activity and accumulation of xenobiotics).

According to the invention the multistage combination preparation for contraception comprises from 2 to 4 first stage daily dosage portions each including an effective amount of at least one natural estrogen as sole active ingredient, from 16 to 22 second stage daily dosage portions each including an effective amount of a combination of at least one natural estrogen and at least one natural or synthetic gestogen as active ingredient; from 2 to 4 third stage daily dosage portions each including an effective amount of at least one natural estrogen as sole active ingredient; and from 2 to 4 final stage daily dosage portions each containing a pharmaceutically acceptable placebo.

In a preferred embodiment of the invention the second stage daily dosage portions are divided into a first group consisting of 3 to 5 daily dosage portions and a second group consisting of 13 to 17 daily dosage portions. The gestogen content of the individual daily dosage portions of the second group is higher than that of the individual daily dosage portions of the first group. Advantageously the gestogen content of the individual portions of the second group amounts to 1.5 to 3 times the gestogen content of the individual portions of the first group. The total number of the administered daily dosages is advantageously 28. Above all estradiols, such as 17β-estradiol, estradiol compounds such as 17β-estradiol valerate from which estradiol is formed after it is taken into the body, conjugate equine estrogens and phytoestrogens are suitable as natural estrogens in the combined preparation according to the invention. Advantageously 19-nortestosterone derivatives, such as desogestrel, dienogest, gestoden and levonorgestrel, and C-21 gestogens, such as medroxyprogesterone acetate, chlormadinone acetate and natural progesterone can be used as the gestogen.

The combination preparation of the invention especially includes combination preparations for oral administration, but also preparations for intravaginal and parenteral administration, in the form of a topical, rectal, intranasal, intrabuccal or sublingual administratable compositions.

The combination preparation according to the invention is prepared in a known manner in a suitable dosage with the conventional solid or liquid carrier materials or diluents and the conventionally used pharmaceutical auxiliary materials according to the desired manner of administration. Tablets, film tablets, pills or hard gelatin capsules may be used in oral administration.

In the combination preparation according to the invention the estrogen-gestogen balance is shifted largely in favor of the estrogen ingredient and in a predetermined stage the gestogen is completely eliminated from the daily dosage. Furthermore this regimen allows an extremely high estrogen daily dosage (more than 4 mg estradiol equivalents/day). The shortening of the time intervals in which a daily dosage is not taken to 2 to 4 days increases both the cycle stability and also the contraceptive protection. The extension of the estrogen stage at the end of the gestogen stage for about 2 to 4 days has no influence on the standard occurrence of the end of bleeding but prevents the incipient follicle growth for the following cycle. The latter result was discovered in subsequent experiments with combinations of estradiol and dienogest. The size of the sonographically measured ovarian follicle never exceeded 10 mm.

The combination preparation according to the invention prevented the gestogen-induced activity of the enzymes, estradiol-17β-dehydrogenase and sulfotransferase, so that the conversion of natural estrogens like that of 17β-estradiol into the less effective estrone occurs to a lesser extent. Because of that sufficient estrogen action in the endometrium is guaranteed, also with natural estrogens. The combination preparation according to the invention has a high reliability as a contraceptive. Because of the use of natural estrogens an accumulation of xenobiotics in the body can be largely prevented by administration of the contraceptive. Natural estrogens also do not have carcinogenic activity.

The invention is now illustrated with a few examples. The improvement of the cyclic bleeding behavior in women is also proven.

EXAMPLES

Example 1

The following regimen was used for administration:

| | |
|---|---|
| 1 to 3 days: | 3 mg estradiol valerate/day |
| 4 to 7 days: | 2 mg estradiol valerate/day + 0.075 mg desogestrel/day |
| 8 to 23 days: | 2 mg estradiol valerate/day + 0.150 mg desogestrel/day |
| 24 to 25 days: | 1 mg estradiol valerate/day |
| 26 to 28 days: | placebo |

The studies were performed on 101 test subjects of ages from 18 to 25 years. The duration of administration amounted to 6 cycles. The average rate of intervening bleeding (bleeding discharge and spotting) dropped from 20.2% in the first administration cycle to 10.7% in the 6th cycle. During the administration no unwanted pregnancy occurred. The serum concentration of progesterone was measured radioimmunologically in 57 test subjects out of 101 on the eighth, twenty second and twenty fourth day of the cycle respectively. A limiting value of 4.0 ng/ml was measured in the fourth cycle during administration only in a few patients. All other measured values were clearly under 2 ng/ml. Thus the reliable ovulation inhibition could be documented using the preparation according to the invention.

Example 2

The following regimen was used for administration:

| | |
|---|---|
| 1 to 3 days: | 3 mg micronized 17β-estradiol/day |
| 4 to 7 days: | 2 mg micronized 17β-estradiol/day + 0.075 mg desogestrel/day |
| 8 to 23 days: | 2 mg micronized 17β-estradiol/day + 0.150 mg desogestrel/day |
| 24 to 25 days: | 1 mg micronized 17β-estradiol/day |
| 26 to 28 days: | placebo |

In contrast to the first example micronized 17β-estradiol was used instead of estradiol valerate. Analogous result to those in Example 1 were obtained in a smaller number of test subjects.

Example 3

The following regimen was used for administration:

| | |
|---|---|
| 1 to 3 days: | 2.5 mg conjugated equine estrogen (CEE)/day |
| 4 to 7 days: | 1.25 mg CEE/day + 1 mg dienogest/day |
| 8 to 23 days: | 1.25 mg CEE/day + 2 mg dienogest/day |
| 24 to 25 days: | 0.60 mg CEE/day |
| 26 to 28 days: | placebo |

In appropriate clinical studies 87 women of age 35 to 47 years were given the contraceptive preparation. The duration of administration amounted to 6 cycles. The intervening bleeding rate (discharge bleeding and spotting) was 15.7% in the first cycle and continuously dropped to 7% in the last cycle during administration. An oral glucose tolerance test was performed in an additional 17 women prior to the beginning of administration and at the end of the 6th cycle studied. In regard to the insulin concentration no variation from the normal range (2 to 25 mU/l) was observed. The insulin/glucose behavior was in the normal range in all test subjects at each measuring time point. The increase of C-peptides was significant. HbA1c shows a significant change between the control cycle and the 6 cycles during administration. The flat glucose values were significantly increased in comparison to the control at the conclusion of testing in 4 test subjects. In oral glucose tolerance tests only 3 test subjects had a reduced glucose tolerance. Two of these 3 test subjects were overweight. The results show that the contraceptive according to the invention based on natural estrogens had an excellent metabolic tolerance.

Example 4

The following regimen was used for administration:

| | |
|---|---|
| 1 to 3 days: | 2.5 mg conjugated equine estrogen (CEE)/day |
| 4 to 7 days: | 1.25 mg CEE/day + 150 mg micronized progesterone/day |
| 8 to 23 days: | 1.25 mg CEE/day + 300 mg micronized progesterone/day |
| 24 to 25 days: | 0.60 mg CEE/ day |
| 26 to 28 days: | placebo |

In this example micronized progesterone is used instead of dienogest as the gestogen component.

Example 5

The following regimen was used for administration:

| | |
|---|---|
| 1 to 3 days: | 3 mg estradiol valerate/day |
| 4 to 7 days: | 1 mg estradiol valerate/day + 1 mg dienogest/day + 0.010 mg ethinyl estradiol/day |
| 8 to 23 days: | 1 mg estradiol valerate/day + 2 mg dienogest/day + 0.010 mg ethinyl estradiol/day |
| 24 to 25 days: | 1 mg estradiol valerate/day |
| 26 to 28 days: | placebo |

In this fifth application example in contrast to the previous examples the entire 20 daily dosages were divided in the second and third stages and indeed in 1 mg natural estrogen complemented by 0.01 mg of synthetic estrogen. In the corresponding clinical studies this multistage preparation was taken by 60 women of age from 18 to 40 years. The study parameters were reliability of contraceptive action (Pearl Index), cycle behavior and compatibility or tolerance. The results were complete suppression of follicle maturation (progesterone blood level determination, sonography) and an outstanding cycle control (intervening bleeding rate dropped from 12.1% in the first cycle to 6% in the final cycle during administration).

The results of these studies proved above all the outstanding good cycle stability of the regimen.

The invention described and claimed herein is also disclosed in German Patent Application 195 40 253.7-41 filed in Germany on Oct. 28, 1995. Priority rights based on the aforesaid German Patent Application are being claimed. The disclosure in the priority document, German Patent Application 195 40 253.7-41, is incorporated in this specification by reference.

While the invention has been illustrated and described as embodied in a combination preparation for contraception based on natural estrogens, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A combination preparation for contraception comprising
    a first stage consisting of two daily dosage portions, each consisting of an effective amount of estradiol valerate;
    a second stage consisting of a first group and a second group of daily dosage portions of a combination of said estradiol valerate and dienogest;
    a third stage consisting of two daily dosage portions, each consisting of an effective amount of said estradiol valerate, wherein said effective amount of said estradiol valerate in each of said two daily dosage portions in said third stage is the same, but smaller than said effective amount of said estradiol valerate in each of said two daily dosage portions in said first stage; and
    an additional stage consisting of two daily dosage portions, each consisting of a pharmaceutically acceptable placebo;

wherein said first group of said daily dosage portions of said second stage consists of five of said daily dosage portions of said combination and wherein said second group of said daily dosage portions of said second stage consists of seventeen of said daily dosage portions of said combination; and wherein respective amounts of said estradiol valerate in each of said daily dosage portions of said second stage are equal and respective amounts of said dienogest in said daily dosage portions of said second group of said second stage are equal to 1.5 to 3 times corresponding amounts of said dienogest in said daily dosage portions of said first group of said second stage.

2. The combination preparation as defined in claim 1, wherein said effective amount of said estradiol valerate in each of said daily dosage portions during said first stage is from 3 to 4 mg/day and said corresponding amounts of said dienogest in said daily dosage portions in said first group of said second stage are minimum amounts necessary for effective contraceptive activity.

3. A combination preparation for contraception consists of a first stage consisting of three daily dosage portions, each consisting of an effective amount of estradiol valerate;

a second stage consisting of a first group and a second group of daily dosage portions of a combination of said estradiol valerate and dienoest;

a third stage consisting of two daily dosage portions, each consisting of an effective amount of said estradiol valerate, wherein said effective amount of said estradiol valerate in each of said two daily dosage portions in said third stage is the same, but smaller than said effective amount of said estradiol valerate in each of said two daily dosage portions in said first stage; and an additional stage consisting of three daily dosage portions, each consisting of a pharmaceutically acceptable placebo;

wherein said first group of said daily dosage portions of said second stage consists of four of said daily dosage portions of said combination and wherein said second group of said daily dosage portions of said second stage consists of sixteen of said daily dosage portions of said combination; and wherein respective amounts of said estradiol valerate in each of said daily dosage portions of said second stage are equal and respective amount of said dienogest in said daily dosage portions of said second group of said second stage are equal to 1.5 to 3 times corresponding amounts of said dienogest in said daily dosage portions of said first group of said second stage.

4. The combination preparation as defined in claim 3, wherein said effective amount of said estradiol valerate in each of said daily dosage portions during said first stage is from 3 to 4 mg/day and said respective amounts of said dienogest in said daily dosage portions in said first group of said second stage is a minimum amount necessary for effective contraceptive activity.

5. The combination preparation as defined in claim 3 or 4, wherein 1 mg of said dienogest is present in each of said daily dosage portions in said first group of said second stage.

* * * * *